United States Patent
Brinser

(10) Patent No.: US 9,132,024 B2
(45) Date of Patent: Sep. 15, 2015

(54) TRIGGER WIRE ACTIVATION LEVER

(75) Inventor: Steven Brinser, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 437 days.

(21) Appl. No.: 13/525,746

(22) Filed: Jun. 18, 2012

(65) Prior Publication Data

US 2012/0323302 A1    Dec. 20, 2012

Related U.S. Application Data

(60) Provisional application No. 61/498,039, filed on Jun. 17, 2011.

(51) Int. Cl.
*A61F 2/06* (2013.01)
*A61F 2/95* (2013.01)

(52) U.S. Cl.
CPC ............ *A61F 2/95* (2013.01); *A61F 2002/9511* (2013.01); *A61F 2002/9517* (2013.01)

(58) Field of Classification Search
CPC .................................. A61F 2/95–2/97; A61F 2002/9505–2002/9665; A61F 2002/011
USPC ................. 606/108, 200; 623/1.11–1.14, 1.23
See application file for complete search history.

(56) References Cited

U.S. PATENT DOCUMENTS

| | | | |
|---|---|---|---|
| 4,586,923 A * | 5/1986 | Gould et al. ................ 604/95.04 |
| 5,749,921 A * | 5/1998 | Lenker et al. ................ 623/1.42 |
| 6,695,875 B2 * | 2/2004 | Stelter et al. ................ 623/1.13 |
| 6,733,521 B2 * | 5/2004 | Chobotov et al. ............ 623/1.12 |
| 7,025,773 B2 | 4/2006 | Gittings et al. |
| 7,122,058 B2 * | 10/2006 | Levine et al. .............. 623/23.65 |
| 7,335,224 B2 * | 2/2008 | Ohlenschlaeger ........... 623/1.11 |
| 7,347,867 B2 | 3/2008 | Phelps et al. |
| 7,357,812 B2 | 4/2008 | Andreas et al. |
| 7,435,253 B1 | 10/2008 | Hartley et al. |
| 7,651,519 B2 | 1/2010 | Dittman |
| 7,666,219 B2 | 2/2010 | Rasmussen et al. |
| 7,722,657 B2 | 5/2010 | Hartley |
| 7,780,717 B2 | 8/2010 | Ducke et al. |
| 7,803,177 B2 | 9/2010 | Hartley et al. |
| 2003/0233140 A1 * | 12/2003 | Hartley et al. ............... 623/1.11 |
| 2006/0004433 A1 | 1/2006 | Greenberg et al. |
| 2007/0167955 A1 * | 7/2007 | Arnault De La Menardiere et al. ............................ 606/108 |
| 2007/0255390 A1 | 11/2007 | Ducke et al. |
| 2008/0109058 A1 | 5/2008 | Greenberg et al. |
| 2008/0269719 A1 * | 10/2008 | Balgobin et al. .............. 604/508 |
| 2008/0294234 A1 | 11/2008 | Hartley et al. |
| 2010/0042118 A1 * | 2/2010 | Garrison et al. .............. 606/148 |
| 2011/0054585 A1 | 3/2011 | Osborne |

* cited by examiner

*Primary Examiner* — Katherine Rodjom
*Assistant Examiner* — Jonathan Hollm
(74) *Attorney, Agent, or Firm* — Brinks Gilson & Lione; Ryan L. Marshall

(57) ABSTRACT

An actuation assembly having at least one lever operably connected to one or more trigger wires which are operably connected to a stent retaining device for a stent graft introducer is disclosed. The lever or levers can be extended or detached from the introducer to remove the trigger wires.

20 Claims, 15 Drawing Sheets

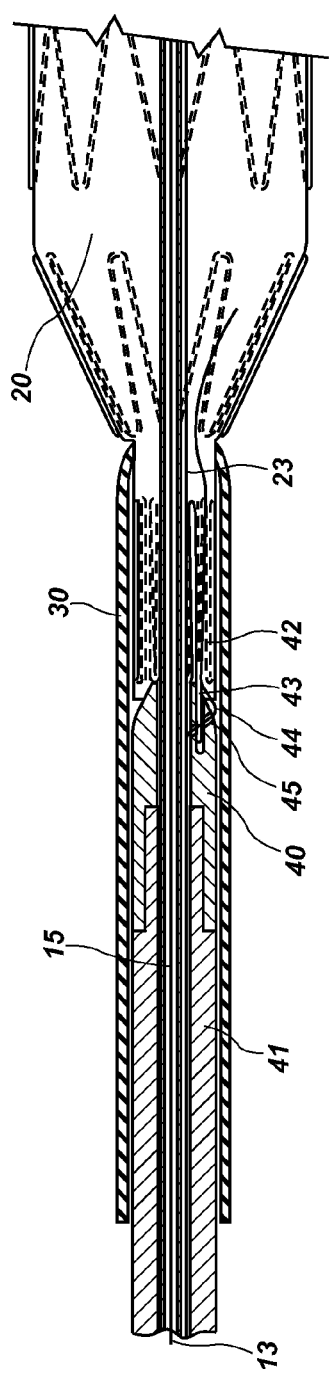
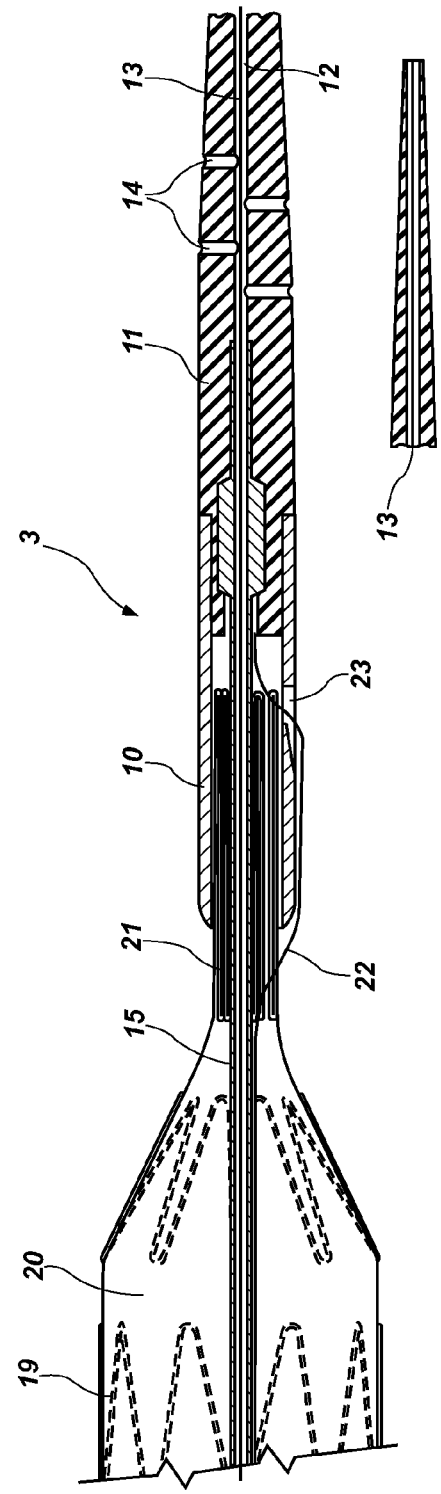
FIG. 8
FIG. 9

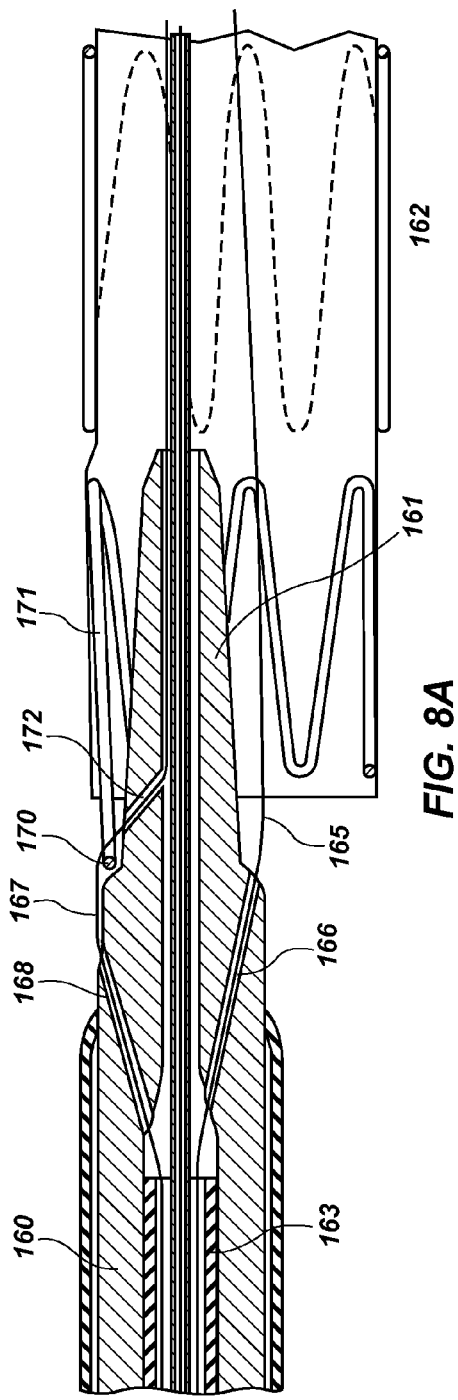
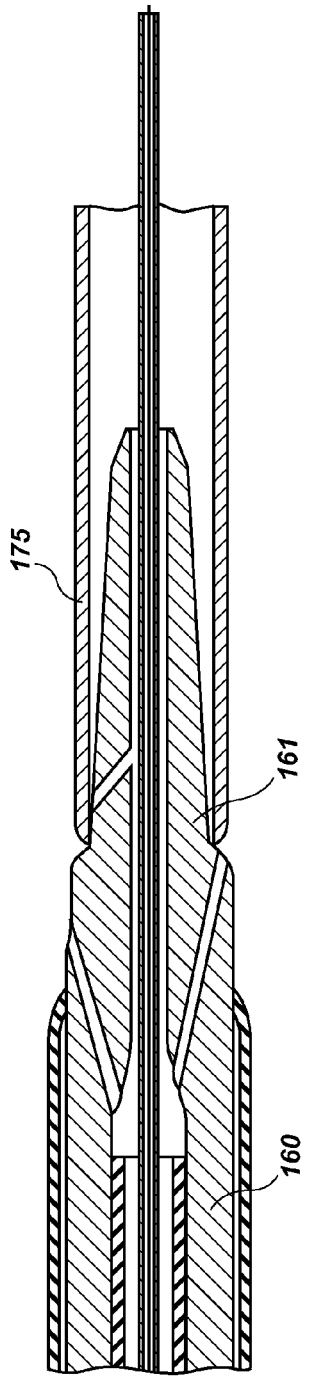
FIG. 8A
FIG. 8B

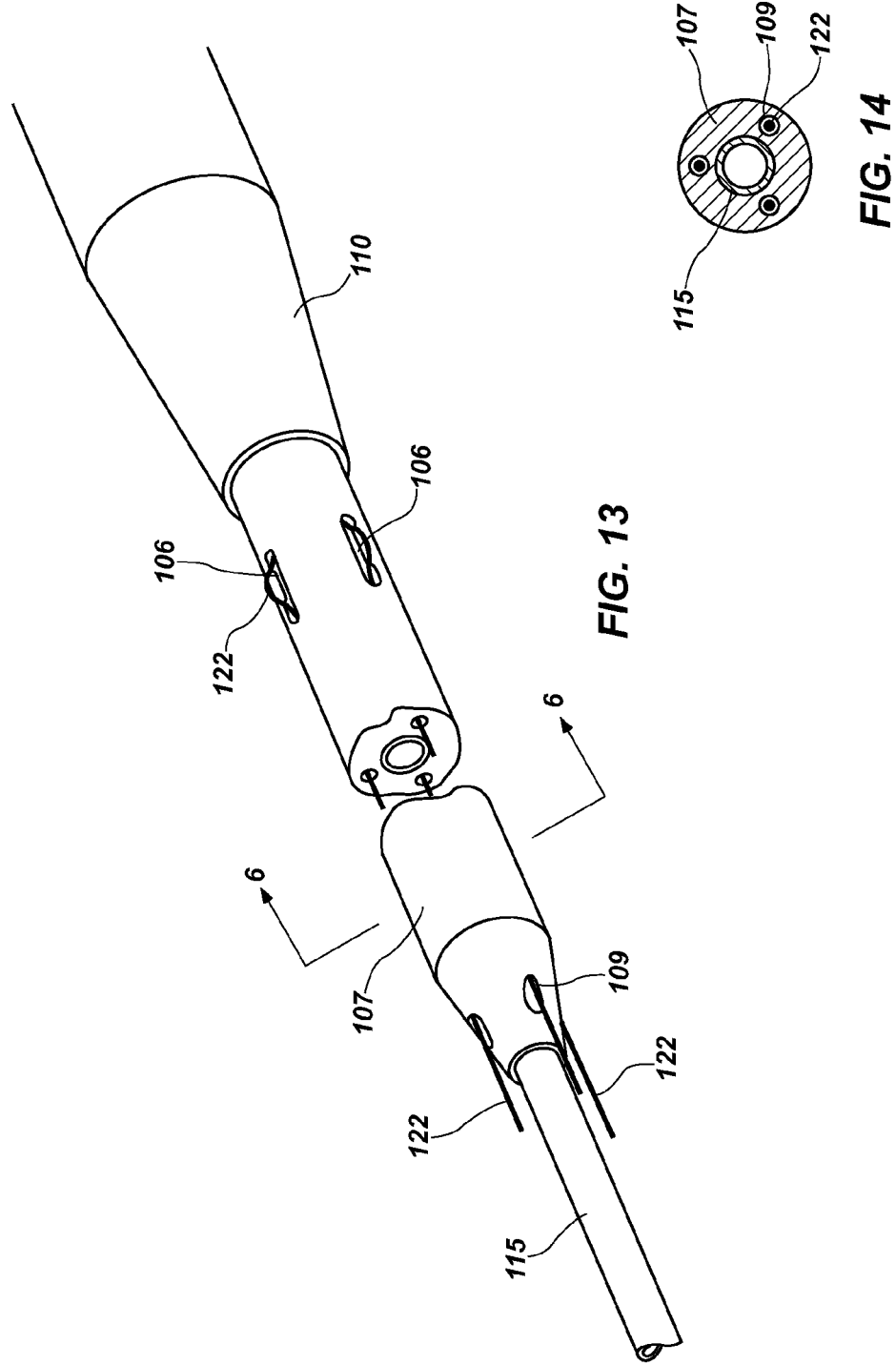

TRIGGER WIRE ACTIVATION LEVER

REFERENCE TO EARLIER FILED APPLICATION

This application claims the benefit under 35 U.S.C. §119(e) of U.S. Provisional Patent Application No. 61/498,039, filed Jun. 17, 2011, and titled "TRIGGER WIRE ACTIVATION LEVER," which is incorporated, in its entirety, by this reference.

TECHNICAL FIELD

The present invention relates to prosthesis deployment and more particularly to controlled, trigger wire deployment devices for endovascular stent grafts and methods of actuating such devices.

BACKGROUND

Deployment devices are used to deploy prostheses and, in particular, prostheses having self-expanding stents within lumens in the human body.

In some forms of prosthesis deployment, device trigger wires are used to restrain a prosthesis in a particular position on a deployment device, for example self-expanding stents in a retracted state. Increasingly complex prosthesis deployment devices incorporate multiple trigger wires, for example 4-6 trigger wires, to afford more control over prosthesis deployment. The force necessary to withdraw the trigger wires increases with the addition of each trigger wire.

It has been found that deployment of stent grafts with multiple trigger wires as well as the general friction of interacting components can provide significant loads on trigger wire actuation mechanisms. Conventional stent delivery devices typically utilize a knob to remove trigger wires for deployment of stent devices. Thus, the force necessary to pull a knob and remove trigger wires becomes increasingly difficult for the operator of the deployment device.

The present disclosure relates to providing a prosthesis deployment system that overcomes at least some of the issues discussed above or at least provides an alternative arrangement of conventional prosthesis deployment systems.

SUMMARY OF THE INVENTION

A prosthesis deployment device is disclosed. The device includes (1) a prosthesis having proximal and distal ends, further including at least one self-expanding stent; (2) a prosthesis retaining device having proximal and distal ends and which is attachable to at least one of the proximal and distal ends of the prosthesis; (3) one or more trigger wires each having a distal end and a proximal end, the proximal ends of the trigger wires being arranged to selectively couple the prosthesis retaining device to at least one of the proximal or distal ends of the prosthesis; and (4) a control mechanism comprising an elongate body member and a lever, wherein the elongate body member has an exterior surface and an interior surface, the interior surface defining a chamber extending longitudinally with the elongate body member, and wherein the lever is pivotally connected to the elongate body member on the exterior surface. At least one of the one or more trigger wire distal ends is operably connected to the lever to selectively disengage the prosthesis retaining device from the prosthesis.

In some embodiments, the elongate body member of the control mechanism includes at least one access passageway extending between the chamber and the lever through which at least one of the one or more trigger wires extends. In some embodiments, the device includes a releasable pivot connection between the lever and the elongate body member.

In some embodiments, the proximal end of at least one trigger wire is connected to the proximal end of the prosthesis retaining device. In some embodiments, the proximal end of at least one trigger wire is connected to the distal end of the prosthesis retaining device. In some embodiments, the one or more trigger wires include a first set of trigger wires and a second set of trigger wires, the first set of trigger wires being operably connected to the proximal end of the prosthesis retaining device and the second set of trigger wires being operably connected to the distal end of the prosthesis retaining device.

In some embodiments, the elongate body member includes two sections, the first section including the lever and the first set of trigger wires, and the second section including a second lever pivotally connected to the elongate body member on the exterior surface. In some embodiments, the device also includes a releasable pivot connection between the second lever and the elongate body member.

In some embodiments, the device includes an external manipulation section, wherein each of the proximal and distal ends of the prosthesis retaining device are attached to the prosthesis in such a manner that the prosthesis can be held in tension therebetween and that each end of the prosthesis can individually be moved in proximal and distal directions.

In some embodiments, the device includes a second elongate body member and a second lever, wherein the second elongate body member has an exterior surface and an interior surface, the interior surface defining a chamber extending longitudinally with the second elongate body member, wherein the chambers of the first and second elongate bodies are in fluid communication, and wherein the second lever is pivotally connected to the second elongate body member on its exterior surface, and wherein the second set of trigger wires is operably connected to the second lever. In some embodiments, the device also includes a releasable pivot connection between the second lever and the second elongate body member.

An intraluminal deployment device is disclosed. The device includes (1) a prosthesis having proximal and distal ends, further comprising at least one self-expanding stent; (2) a prosthesis retaining device having proximal and distal ends and which is attachable to at least one of the proximal and distal ends of the prosthesis; (3) a plurality of trigger wires each having a distal end and a proximal end, the proximal ends of the trigger wires being arranged to selectively couple the prosthesis retaining device to at least one of the proximal or distal ends of the prosthesis; (4) a control mechanism comprising an elongate body member and a lever, wherein the elongate body member has an exterior surface and an interior surface, the interior surface defining a chamber extending longitudinally with the elongate body member, and wherein the lever is releasably and pivotally connected to the elongate body member on the exterior surface. The distal ends of the plurality of trigger wires are operably connected to the lever to selectively disengage the prosthesis retaining device from the prosthesis.

A trigger wire release mechanism for releasing one or more retained ends of a prosthesis is disclosed. The trigger wire mechanism includes a prosthesis retaining device arranged to engage at least one end of the prosthesis, one or more trigger wires each having a distal end and a proximal end, the proximal end being arranged to selectively couple the prosthesis retaining device to the prosthesis, a control mechanism comprising an elongate body member and a lever, wherein the elongate body member has an exterior surface and an interior surface, the interior surface defining a chamber extending longitudinally with the elongate body member, and wherein the lever is pivotally connected to the elongate body member on the exterior surface and wherein each of the one or more trigger wire distal ends are operably connected to the lever member to selectively disengage the prosthesis retaining device from the prosthesis.

In some embodiments, the elongate body member of the control mechanism includes at least one access passageway extending between the chamber and the lever through which each of the one or more trigger wires extends.

In some embodiments, the trigger wire release mechanism includes a releasable pivot connection between the lever and the elongate body member.

In some embodiments, the prosthesis retaining device has a proximal end and a distal end. In some embodiments, the proximal end of the one or more of the trigger wires are connected to the proximal end of the prosthesis retaining device. In some embodiments, the proximal end or end of the one or more of the trigger wires are connected to the distal end of the prosthesis retaining device.

In some embodiments, the one or more trigger wires include a first set of trigger wires and a second set of trigger wires, the first set of trigger wires being operably connected to the proximal end of the prosthesis retaining device and the second set of trigger wires being operably connected to the distal end of the prosthesis retaining device.

In some embodiments, the elongate body member includes two sections, the first section comprising the lever and the first set of trigger wires, and the second section comprising a second lever pivotally connected to the elongate body member on the exterior surface.

In some embodiments, the elongate member has a proximal end and a distal end. In some embodiments, the lever is attached to the proximal end of the elongate member. In some embodiments, the lever is attached to the distal end of the elongate member.

In some embodiments, a first lever is attached to a proximal end of the elongate member, and a second lever is attached to the distal end of the elongate member.

In some embodiments, the trigger wire release mechanism also includes a second elongate body member and a second lever, wherein the second elongate body member has an exterior surface and an interior surface, the interior surface defining a chamber extending longitudinally with the second elongate body member, wherein the chambers of the first and second elongate bodies are in fluid communication, and wherein the second lever is pivotally connected to the second elongate body member on its exterior surface, and wherein the second set of trigger wires is operably connected to the second lever.

DETAILED DESCRIPTION

Throughout this specification, the terms proximal and proximally are used for a position or direction towards the patient's heart, and the terms distal and distally are used for a position or direction away from the patient's heart. When applied to other vessels, corresponding terms such as caudal and cranial should be understood.

The construction of embodiments and the methods by which the devices disclosed herein may be operated may be made clearer with the aid of the accompanying drawings. For clarity, the lumens or vessels into which the prosthesis is inserted are not shown in the drawings.

In the drawings:

FIG. 8 shows that part of the introducer around the distal end of the prosthesis in detail;

FIG. 8A shows an alternative embodiment of that part of the introducer around the distal end of the prosthesis in detail;

FIG. 8B shows the embodiment of FIG. 8A with the distal attachment device advanced to the proximal attachment device;

FIG. 9 shows that part of the introducer around the proximal end of the prosthesis in detail;

FIG. 13 shows a detail of part of an alternate embodiment with a deployment device having a trigger wire guide and a plurality of trigger wires;

FIG. 14 shows a transverse cross section of the trigger wire guide and plurality of trigger wires along the line 6-6' shown in FIG. 13;

Figure 1:
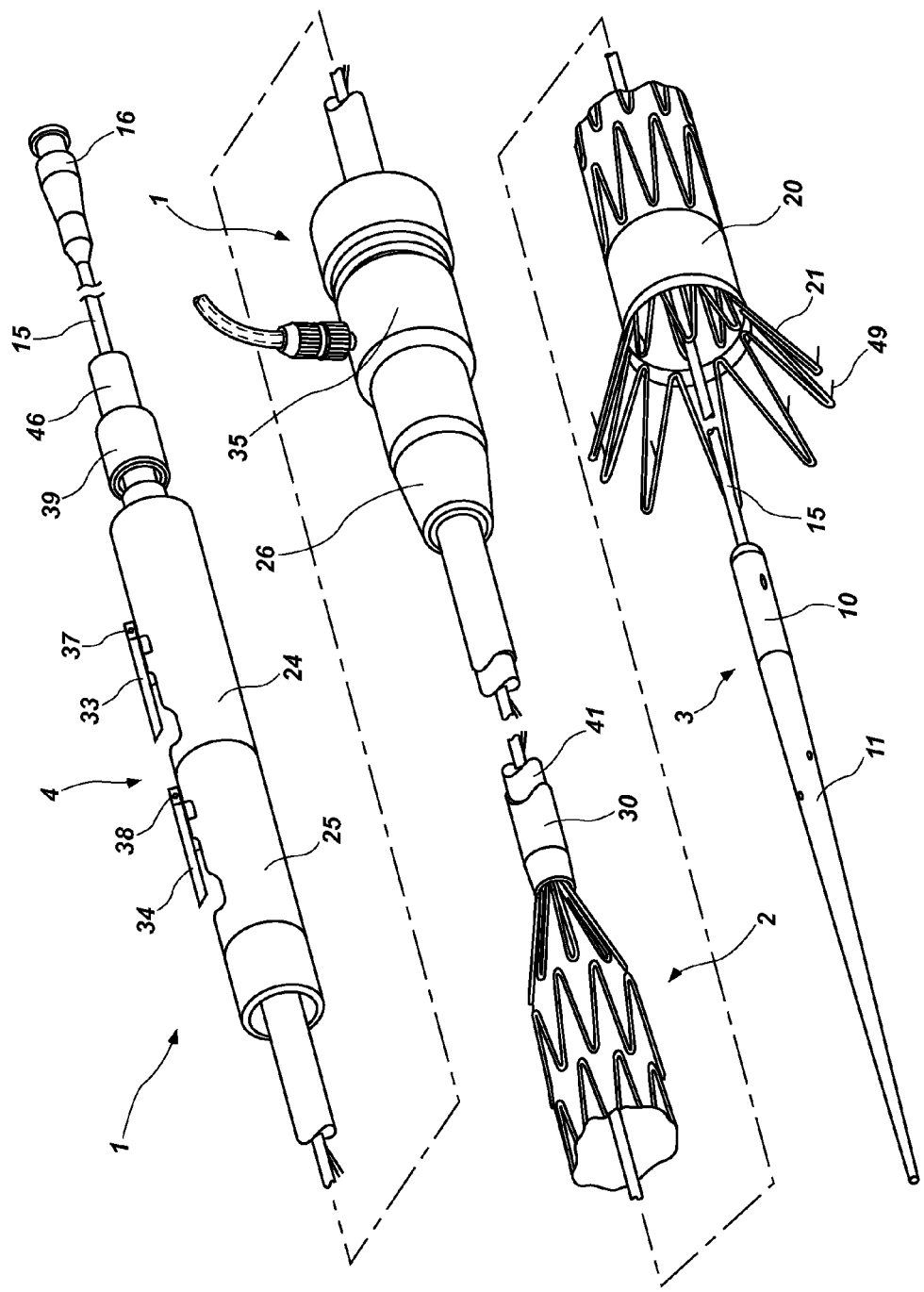
FIG. 1 shows a first embodiment of an introducer in perspective view with the prosthesis partially deployed.

Now referring more closely to the drawings and particularly to the embodiments shown in FIGS. 1-12, it will be seen that an endovascular arrangement of a device including an introducer comprises generally an external manipulation section 1, a distal attachment region 2 and a proximal attachment region 3.

The proximal attachment region 3 shown in detail in FIG. 9 includes a cylindrical sleeve 10 (sometimes referred to as a proximal attachment means) with a long tapered flexible extension 11 extending from its proximal end. The extension 11 has an internal longitudinal aperture 12 to enable it to be advanced along an insertion wire 13 (sometimes referred to as a guidewire or guide wire) and to enable the supply of medical reagents such as a contrast agent to allow angiography to be performed during placement and deployment phases of a medical procedure involving the device. A thin-walled tube 15 is fastened to the extension 11 and extends through the complete introducer to the manipulation section and terminates in a connection means 16 (FIG. 1) for a syringe so that one or more medical reagents may be introduced into the tube and subsequently into the extension 11 to emanate through the apertures 14. The thin-walled tube 15 is flexible so that the introducer can be advanced along a relatively tortuous vessel such as the femoral artery and also to allow manipulation longitudinally and rotationally of the proximal attachment region 3.

Figure 11:
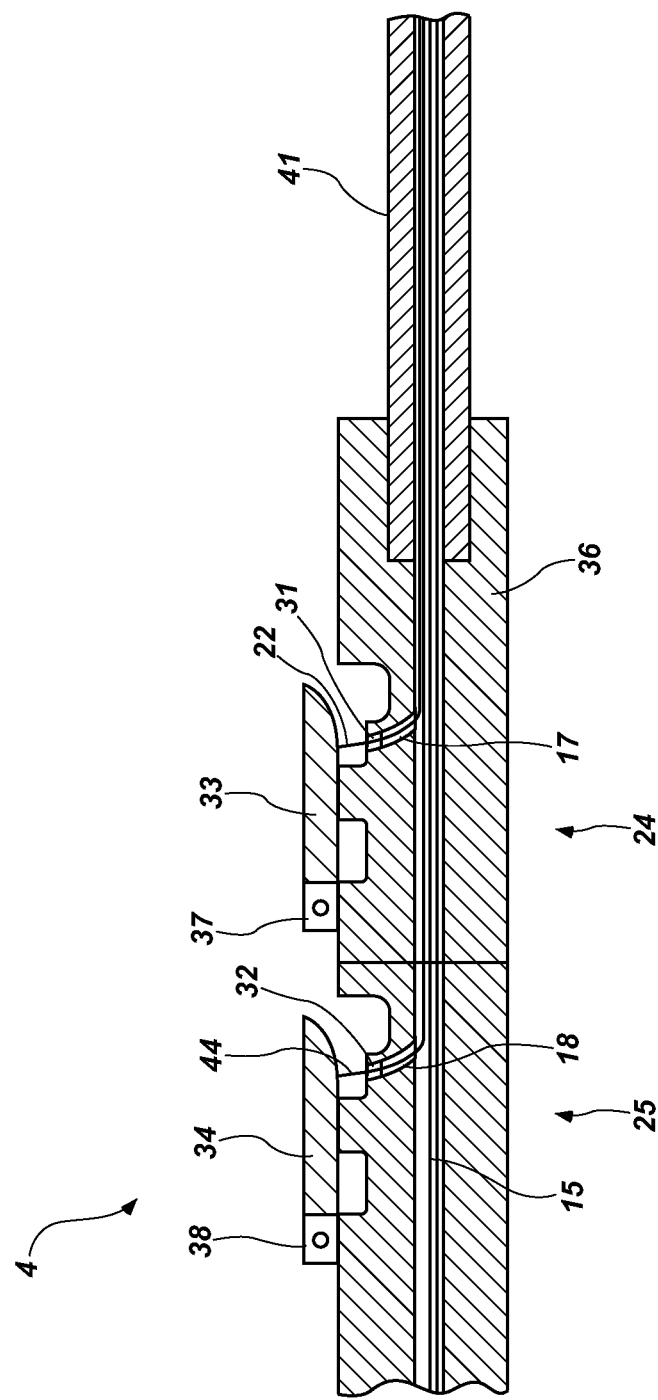
FIG. 11 shows that part of the introducer around the trigger wire release mechanisms in detail.

The prosthesis 20 is of a self-expanding type having resilient stents 19 to enable it to expand after it is released from the introducer. The prosthesis retained within the introducer includes a self-expanding zigzag stent 21 extending from its proximal end. In the compressed condition, the zigzag stent 21 is retained in the cylindrical sleeve 10 of the proximal attachment region 3, and is retained therein by means of a trigger wire 22 which extends through an aperture 23 in the side of the cylindrical sleeve 10 and is received in one of the loops of the zigzag stent. The trigger wire 22 extends along most of the length of the introducer and exits at the manipulation region at a proximal wire release mechanism 24 (FIGS. 1 and 11).

Figure 2:
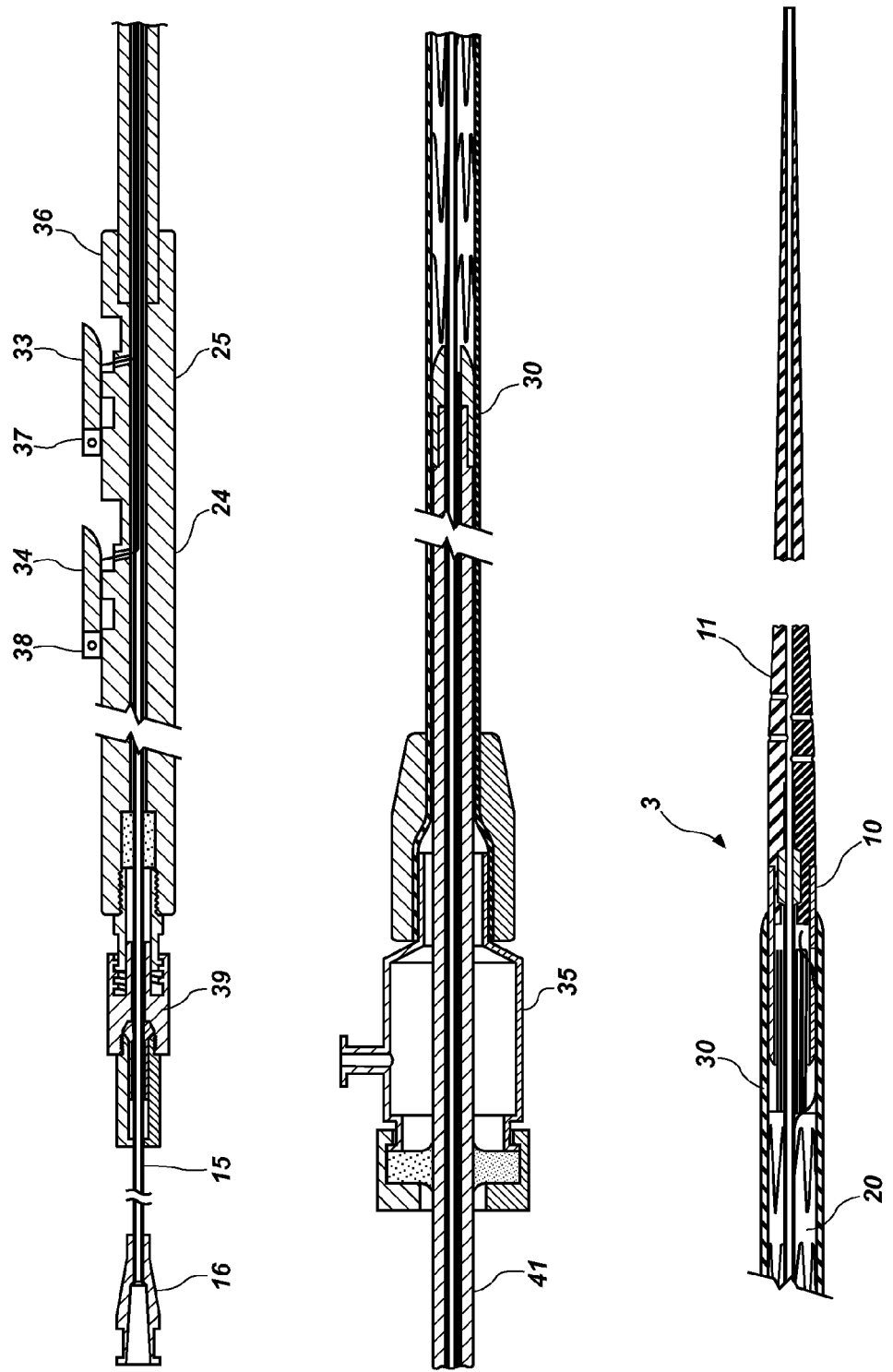
FIG. 2 shows the first embodiment of the introducer as shown in FIG. 1 being fully loaded and ready for introduction into a patient.

The prosthesis 20 is retained in its compressed condition by means of an external sleeve 30 (sometimes referred to as a sheath) which is advanced to be received over the cylindrical sleeve 10 when the device is assembled for insertion as can be particularly seen in FIG. 2. The external sheath 30 extends distally to external of a patient to the external manipulation section 1 and a gripping and haemostatic sealing means 35 thereof.

As can be particularly seen in FIG. 8, the distal end of the prosthesis 20 is retained in the distal attachment device 40 which is mounted onto a thick-walled tube 41 which extends distally to external of the patient and to the manipulation region 1. The thick walled tube 41 is coaxial with and radially outside the thin-walled tube 15 and the external sleeve 30 is coaxial with and radially outside the thick-walled tube 41. The distal end 42 of the prosthesis 20 has a loop 43 through which a distal trigger wire 44 extends. The distal trigger wire 44 extends through an aperture 45 on the distal attachment device into the annular region between the thin-walled tube 15, and the thick-walled tube 41 like the proximal trigger wire which also extends through the annular space between the thick-walled tubing 41 and the thin-walled tubing 15 to the manipulation device and out at a distal wire release mechanism 25 as depicted in FIGS. 2 and 11.

In an alternative embodiment shown in FIGS. 8A and 8B, the thick-walled tube 160 has a tapered end 161 through which the thin-walled tube 162 extends. A low-friction lining 163 is provided between the thick-walled tube 160 and the thin-walled tube 162 so that the former slides easily over the latter. The proximal trigger wire 165 and the distal trigger wire 167 are within the thick-walled tube 160 and extend out from respective apertures 166 and 168 distal of the tapered end 161. The distal trigger wire 167 passes through the loop 170 in the distal end of the prosthesis 171 and re-enters the tapered portion 161 through aperture 172.

As shown in FIG. 8B, when the distal attachment region has been advanced to the proximal attachment region, the tapered portion 161 fits into the tube 175 to provide a smooth surface for the retraction of the two together.

Figure 10:
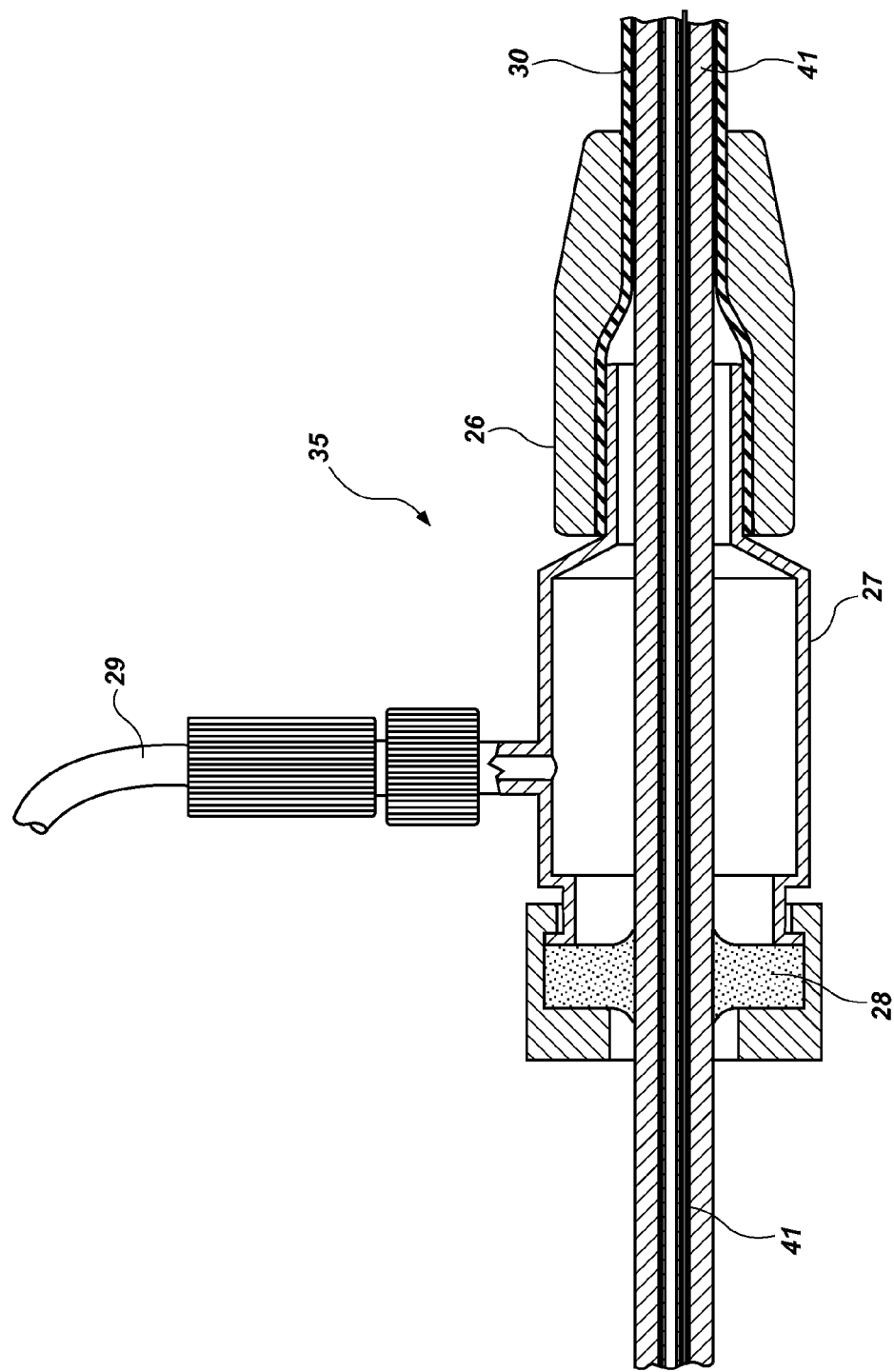
FIG. 10 shows that part of the introducer around the haemostatic seal in detail.

As can be particularly seen in FIG. 10, the haemostatic sealing means 35 which remains external of a patient in use has a clamping collar 26 which clamps the external sleeve 30 to the haemostatic seal 27. The haemostatic seal 27 has a silicone seal ring 28 to seal against the thick-walled tubing 41 to provide the haemostatic seal and a side tube 29 for the introduction of medical reagents between the thick-walled tubing 41 and the external sleeve 30.

As can be particularly seen in FIG. 11, the trigger wire actuation section 4 of the external manipulation section 1 has a body 36 into the end of which is mounted the thick-walled tubing 41 and through which passes the thin-walled tube 15.

Both the proximal wire release mechanism 24 and the distal wire release mechanism 25 include the body 36. Each wire release mechanism includes a lever 33 and 34 through pivotal connections 37 and 38 respectively. Haemostatic seals 31 and 32 are provided so the respective trigger wires 22 and 44 can extend out through the body 36 through access passages 17 and 18 to levers 33 and 34.

Figure 12:
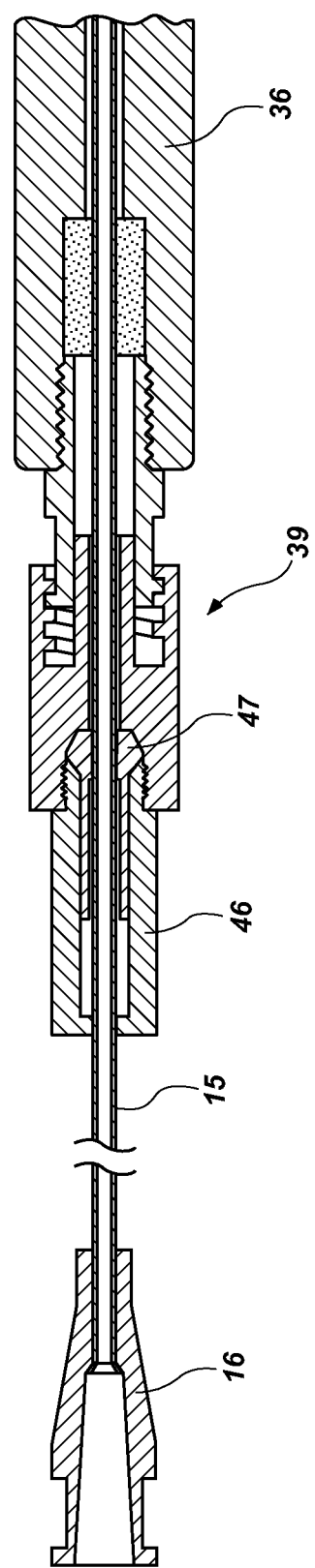
FIG. 12 shows that part of the introducer around the pin vise clamp and the medical reagent introduction tube in detail.

As can be particularly seen in FIG. 12, there is a pin vise 39 mounted onto the other end of the body 36 from the thick-walled tube 41. The pin vise 39 has a screw cap 46 which when screwed in, clamps vise jaws 47 against the thin-walled tube 15, so that the thin-walled tube 15 can only move with the body 36 and, consequently, the thin-walled tube 15 can only move with the thick-walled tube 41. With the clamp tightened, the entire assembly, except the external sleeve 30, can be moved as one.

In an alternative embodiment, the device may include multiple trigger wires for actuating the proximal end of a prosthesis and multiple trigger wires for actuating the distal end of a prosthesis. Referring to FIGS. 13-16, a part of the prosthesis deployment device is shown and includes the thin-walled tube 115 which extends the length of the deployment device. At the proximal end of the thin-walled tube 115 is a cylindrical sleeve 110.

Extending distally from the cylindrical sleeve 110 and surrounding the thin-walled tube 115 is a trigger wire guide 107. The trigger wire guide 107 is coaxial with the thin-walled tube 115 and includes in this embodiment three lumens 109 through which, in use, pass trigger wires 122.

Figure 15:
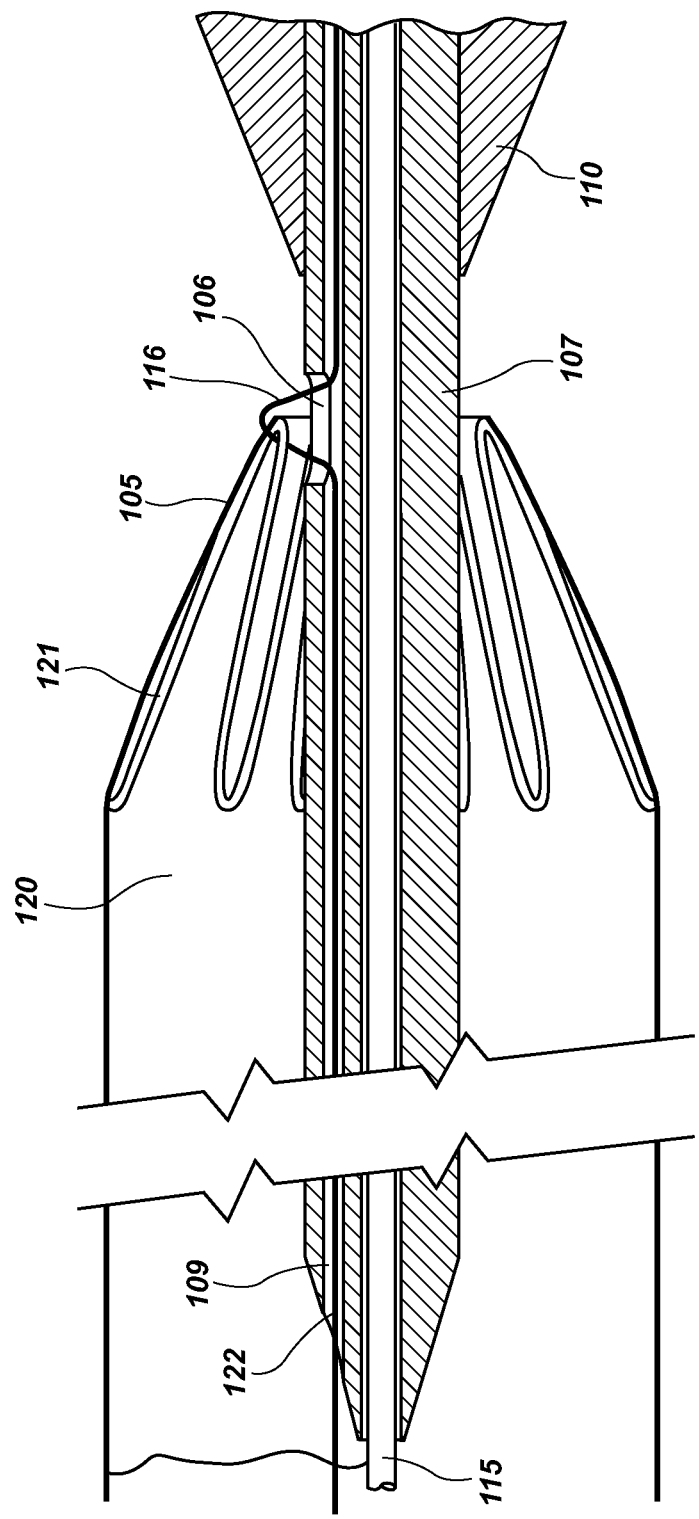
FIG. 15 shows a cross sectional view of a an alternate embodiment of a deployment device having a trigger wire guide and a plurality of trigger wires for retaining the self expanding stents of a prosthesis.

Just distal of the tapered flexible extension 111 (not shown), there are apertures 106 in the trigger wire guide 107 extending into each lumen 109 and out of which aperture 106 extends the trigger wire 122 in a loop 116 so that it can engage the zig zag stents 121 of a prosthesis 120 (see FIG. 15). The trigger wires 122 continue along the lumen 109 to terminate within the region of the cylindrical sleeve 110. When it is desired to release the stent 121, then the trigger wires 122 are pulled out as is discussed in relation to FIGS. 2-4.

The alternate embodiment prosthesis is also shown in FIG. 15. In this embodiment, the proximal stent 121 of the prosthesis 120 is a covered stent. Each trigger wire 122 in its loop 116 passes through the stent and graft material 105. In embodiments lacking a covering, each trigger wire 122 in its loop 116 passes through the stent but not the graft material.

Figure 16:
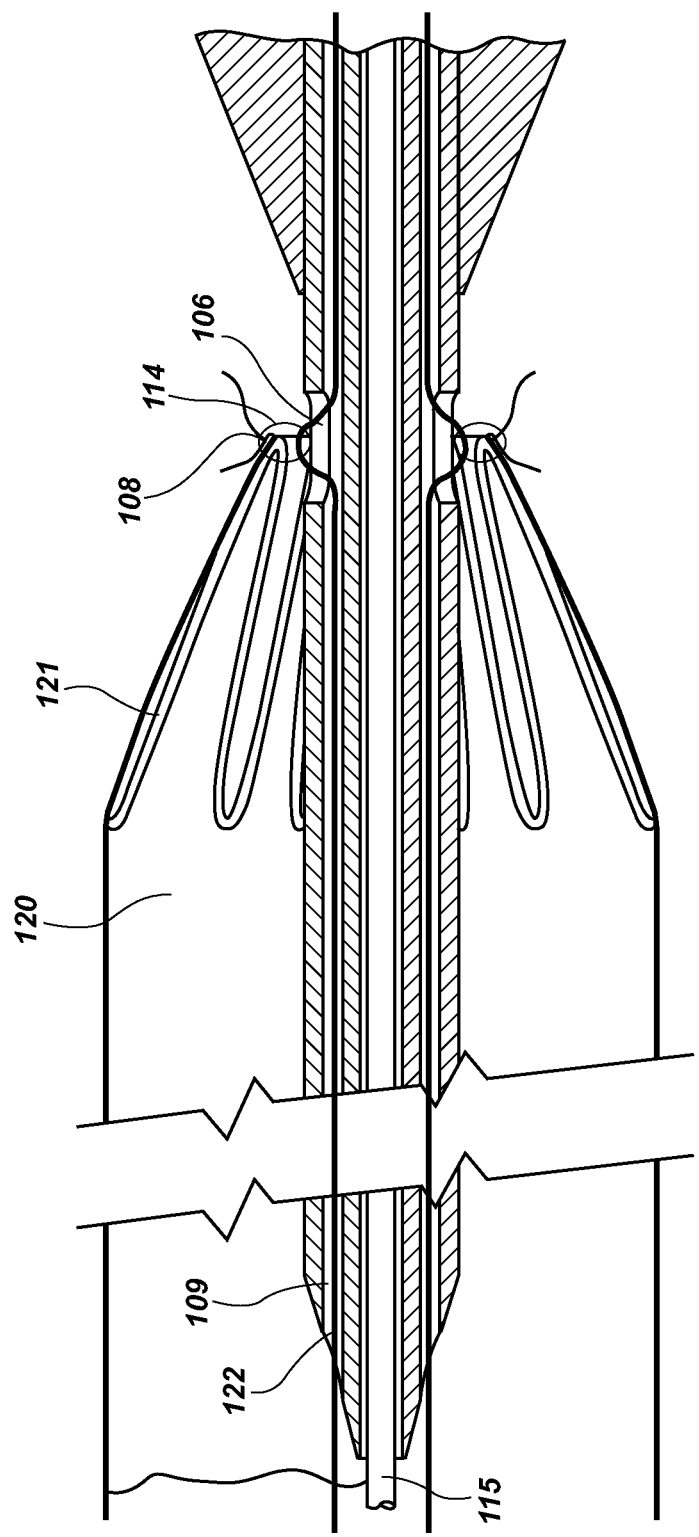
FIG. 16 shows a similar view to FIG. 15 but with a different method of retaining the self expanding stents of the prosthesis.

As an alternative to the use of the loop 116 to engage directly into the stent and graft material the arrangement as shown in FIG. 16 can be used. In FIG. 16, a piece of thread 114, such as a monofilament or woven suture material, is used with a loop around a trigger wire 122, the stent 121 and the graft material 105 with a knot 108. The stent 121 and the graft material 105 are released from the trigger wires 122 when the trigger wires are actuated and withdrawn. In such a situation the loop of thread 114 would stay attached to the stent 121 or the graft material 105.

In another embodiment (not shown), the trigger wire release section has a single lever to which one or more trigger wires are attached. In one embodiment, the lever is connected to one or more trigger wires which connect to the cylindrical sleeve for deployment of the proximal region of a prosthesis. In another embodiment, the lever is connected to one or more trigger wires which connect to the distal wire release mechanism. In yet another embodiment, the lever is connected to a plurality of trigger wires a portion of which connect to the cylindrical sleeve and the remaining trigger wire or wires connect to the distal wire release mechanism.

Where more than one trigger wire extends from a lever to a proximal or distal region of a prosthesis, the trigger wires may pass through a trigger wire guide. Alternatively, where more than one trigger wire extends from a lever to a proximal or distal region of a prosthesis, the trigger wires may be bundled until reaching a region just distal of their connection to the prosthesis.

A trigger wire or plurality of trigger wires may be connected to the lever through a variety of connection means including adhesive or fusion welds, knots, hoop and eyelet, and the like.

Returning to FIGS. 2 to 7, these figures show the various stages of the deployment of the prosthesis according to one embodiment. A method for deploying a prosthesis using the prosthesis delivery device described herein will now be explained.

A guide wire (not shown) is introduced into the femoral artery and advanced until its tip is above the region into which the prosthesis is to be deployed.

In FIG. 2, the introducer assembly is shown fully assembled ready for introduction into a patient. The prosthesis 20 is retained at each of its ends by the proximal and distal retaining assemblies respectively and compressed by the external sleeve 30. If an aortic aneurism is to be grafted, for example, the introducer assembly can be inserted through a femoral artery over the guide wire in the form as shown in FIG. 2 and positioned by radiographic techniques (not discussed here).

Figure 3:
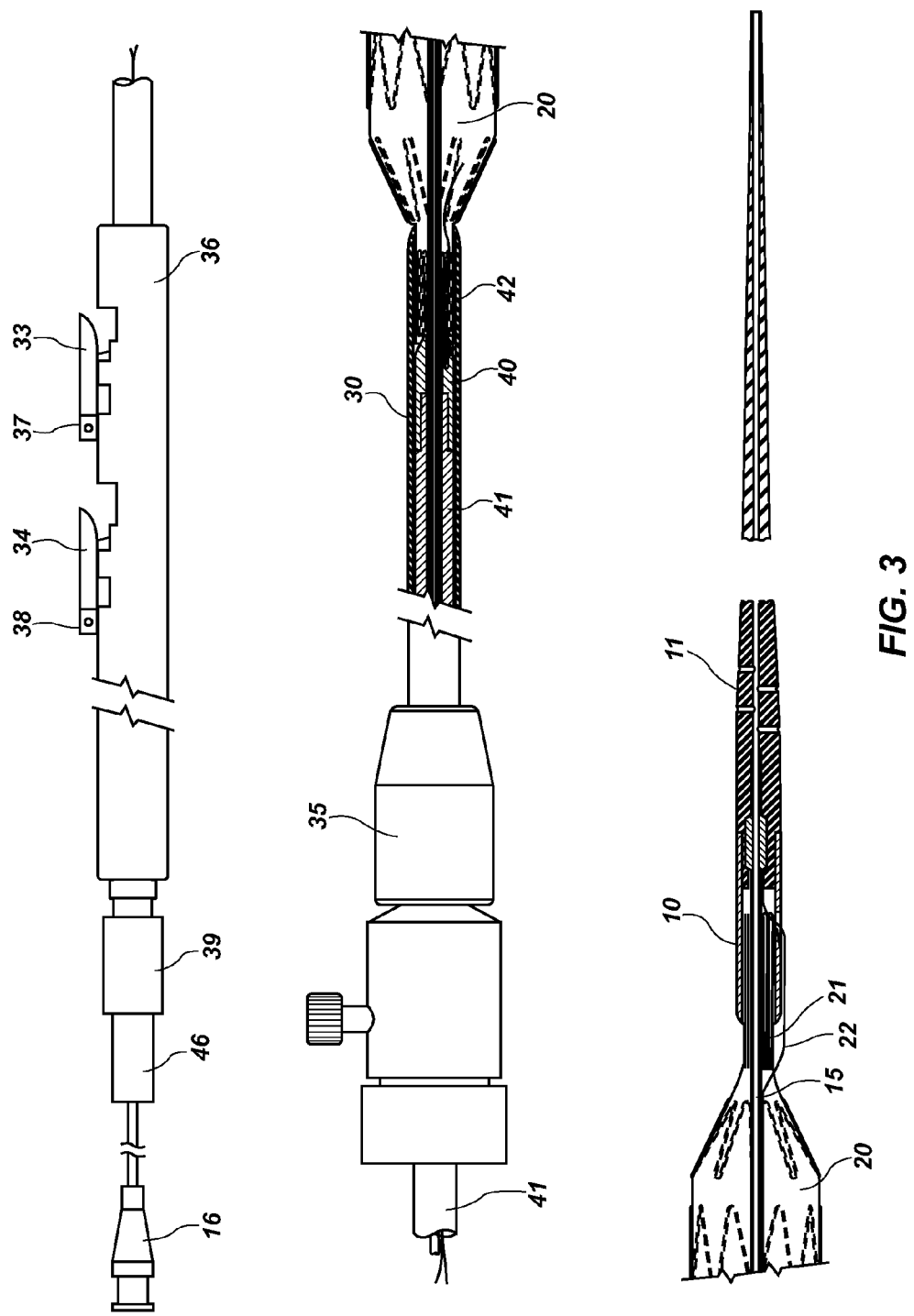
FIG. 3 shows the embodiment of FIG. 2 in the next stage of deployment of the prosthesis.

In FIG. 3, it will be seen that once the introducer assembly is in a selected position the external sleeve 30 is withdrawn to just proximal of the distal attachment device 40, so that the prosthesis 20 is now released. Once released, it can radially expand except where the most proximal zigzag stent 21 is still retained within the proximal attachment device 10 and where its distal end 42 is retained within the external sheath 30.

By release of the pin vise 39, small movements of the thin-walled tubing 15 are allowed with respect to the thick-walled tubing 41, and the prosthesis 20 may be lengthened or shortened or rotated or compressed to accurately position the prosthesis in the desired place within the body lumen. X-ray opaque markers (not shown) may be placed at known locations along the prosthesis to assist with placement of the prosthesis.

Figure 4:
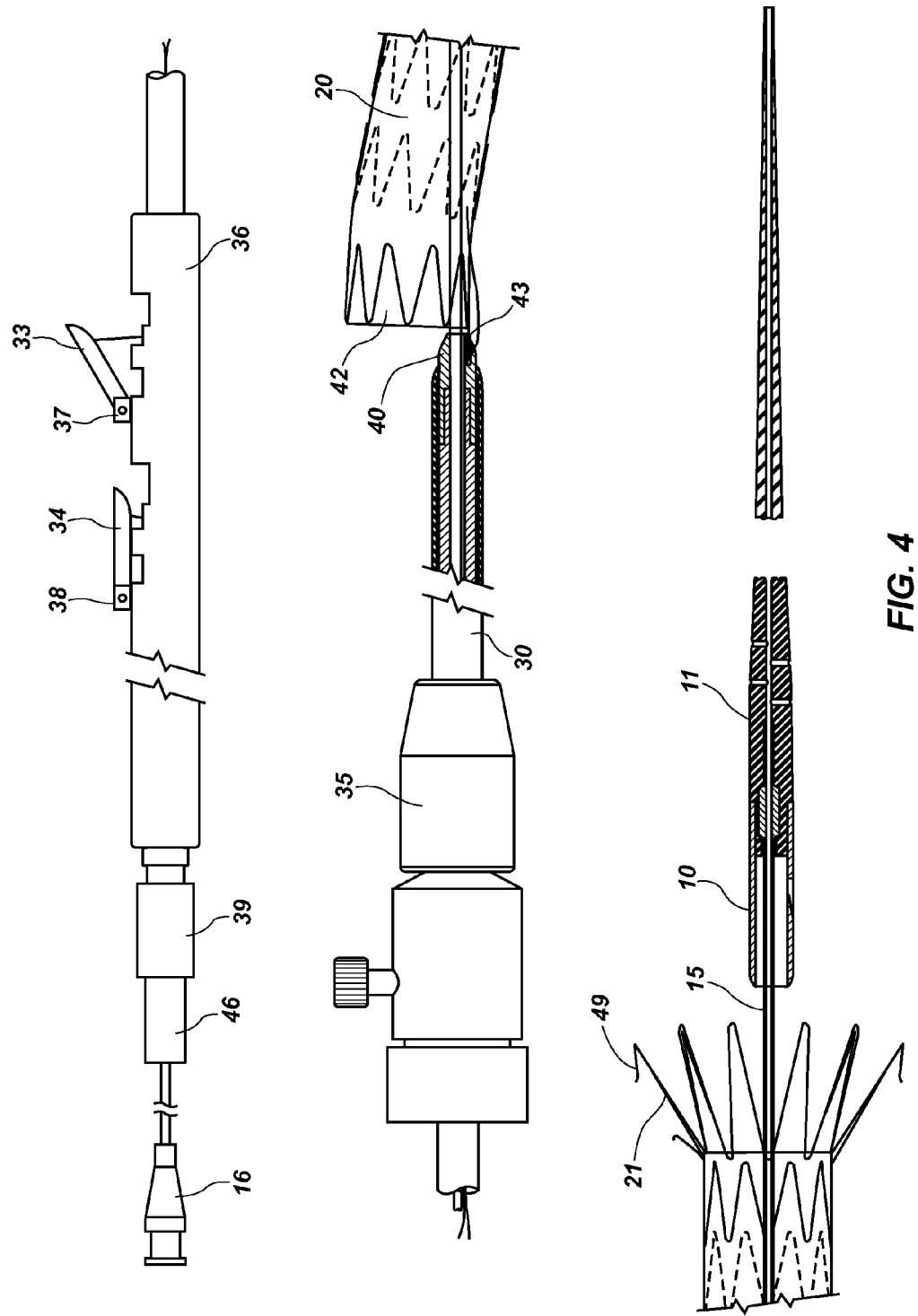
FIG. 4 shows the embodiment of FIG. 2 with the release of the proximal end stage of deployment.

In FIG. 4, the proximal trigger wire 22 (FIG. 3) has been withdrawn by actuation of the proximal wire release mechanism 24 (FIG. 3). Extension of the lever 33 away from the body 36 can actuate withdrawal of the proximal trigger wire 22. Optionally, after extending the lever 33 from the body 36, pivotal connection 37 may be disengaged allowing the operator to manipulate the lever 33 as a handle-like implement so as to remove trigger wire 22 entirely from the device. At this stage lever 33 and the proximal trigger wire 22 have been removed completely.

The screw cap 46 of the pin vise 39 is then loosened so that the thin-walled tubing 15 can been pushed in a proximal direction to move the cylindrical sleeve 10 in a proximal direction thereby releasing the zigzag stent 21 at the proximal end of the prosthesis from the cylindrical sleeve 10. At this stage, the hooks or barbs 49 on the zigzag stent 21 grip into the walls of a lumen (not shown) to hold the prosthesis therein. From this stage forward, the proximal end of the prosthesis cannot be moved again.

The distal end 42 of the prosthesis is still retained by the distal attachment device 40 with the loop 43 retained therein. The external sheath 30 has been withdrawn to a position distal of the distal attachment device 40 to allow the distal end of the attachment device to expand.

At this stage, however, the distal end of the prosthesis can still be moved so that the prosthesis can be rotated, lengthened or shortened, or otherwise moved to accurately position the prosthesis. Where the prosthesis to be deployed is a bifurcated graft, for example, the movement at this stage can ensure that the shorter leg is directed in the direction of the contra-iliac artery.

Figure 5:
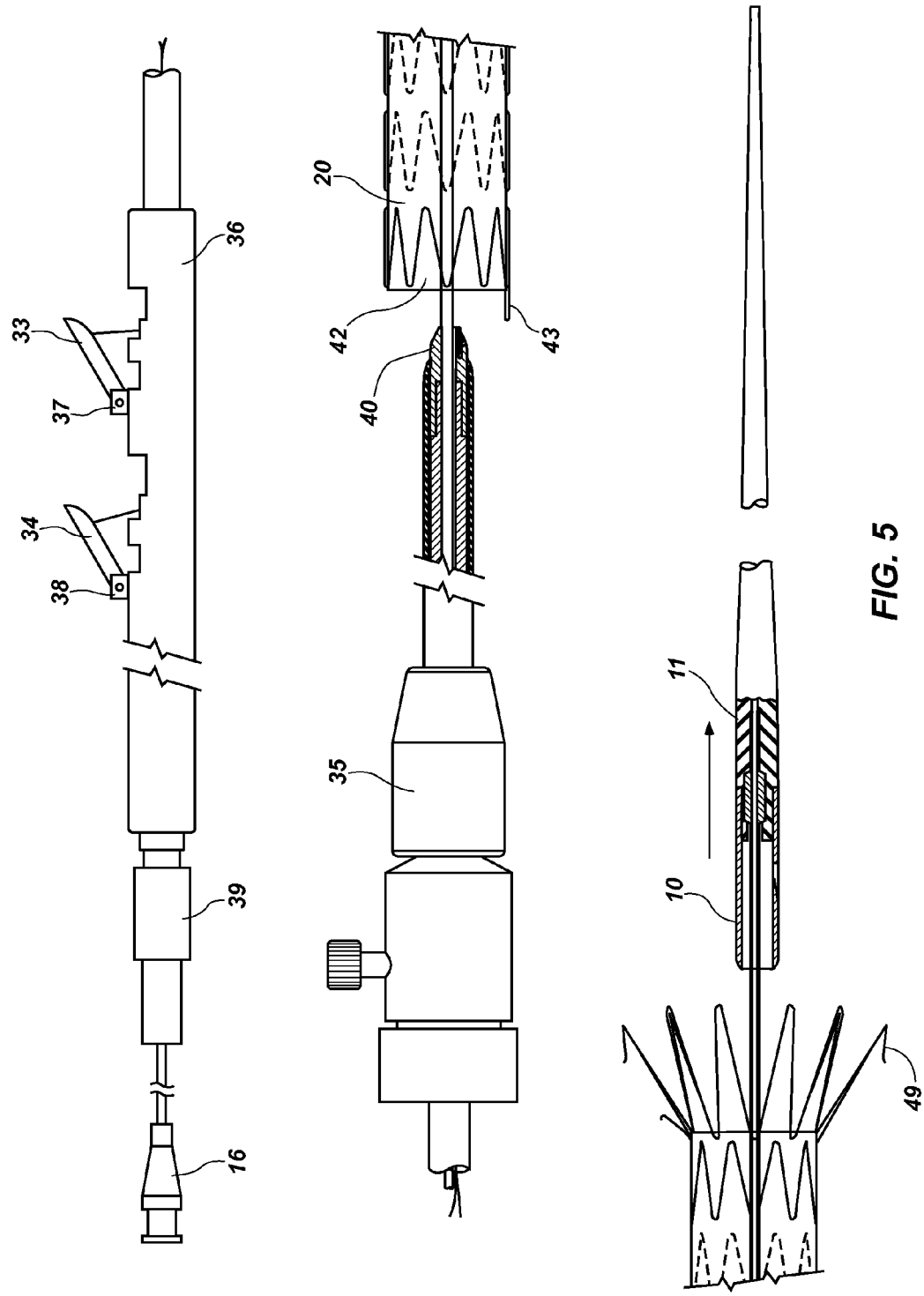
FIG. 5 shows the release of the distal end stage of deployment.

In FIG. 5, the distal end 42 of the prosthesis has been released by removal of the distal trigger wire 44 by actuation of the distal wire release mechanism 25. Extension of the lever 34 away from the body 36 can actuate withdrawal of the distal trigger wire 44. Optionally, after extending the lever 34 from the body 36, pivotal connection 38 may be disengaged allowing the operator to manipulate the lever 34 as a handle-like implement so as to remove trigger wire 44 entirely from the device (not shown). At this stage lever 34 and the proximal trigger wire 44 have been removed completely. The loop 43 of the terminal distal zigzag stent is hence freed and the prosthesis is now free to expand to the walls of the vessel and the introducer can be removed. Similarly, after extending the lever 33 from the body 36, pivotal connection 37 may be disengaged allowing the operator to manipulate the lever 33 as a handle-like implement so as to remove trigger wire 22 entirely from the device (not shown).

Figure 6:
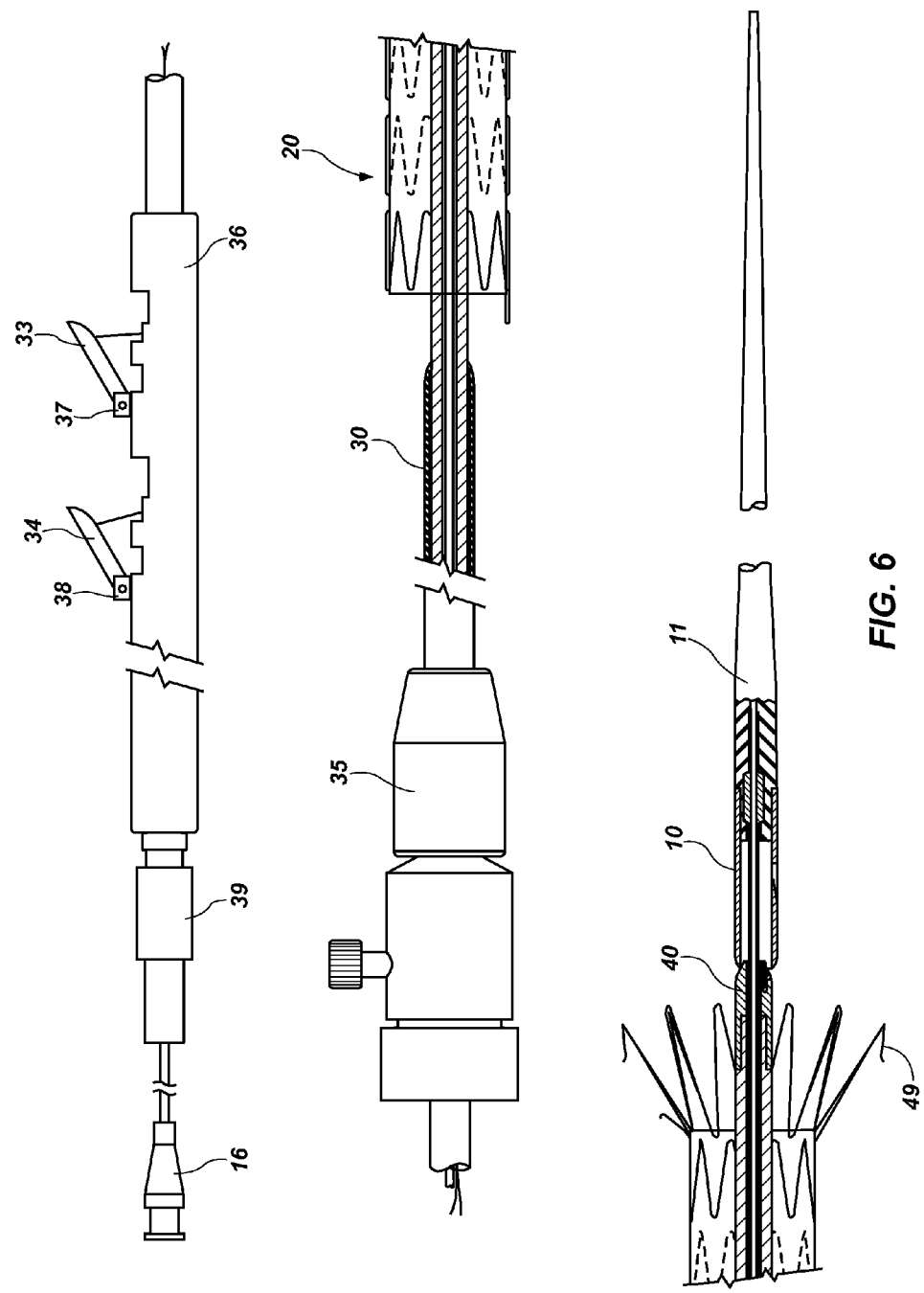
FIG. 6 shows the advancement of the distal attachment device to the proximal attachment device.
Figure 7:
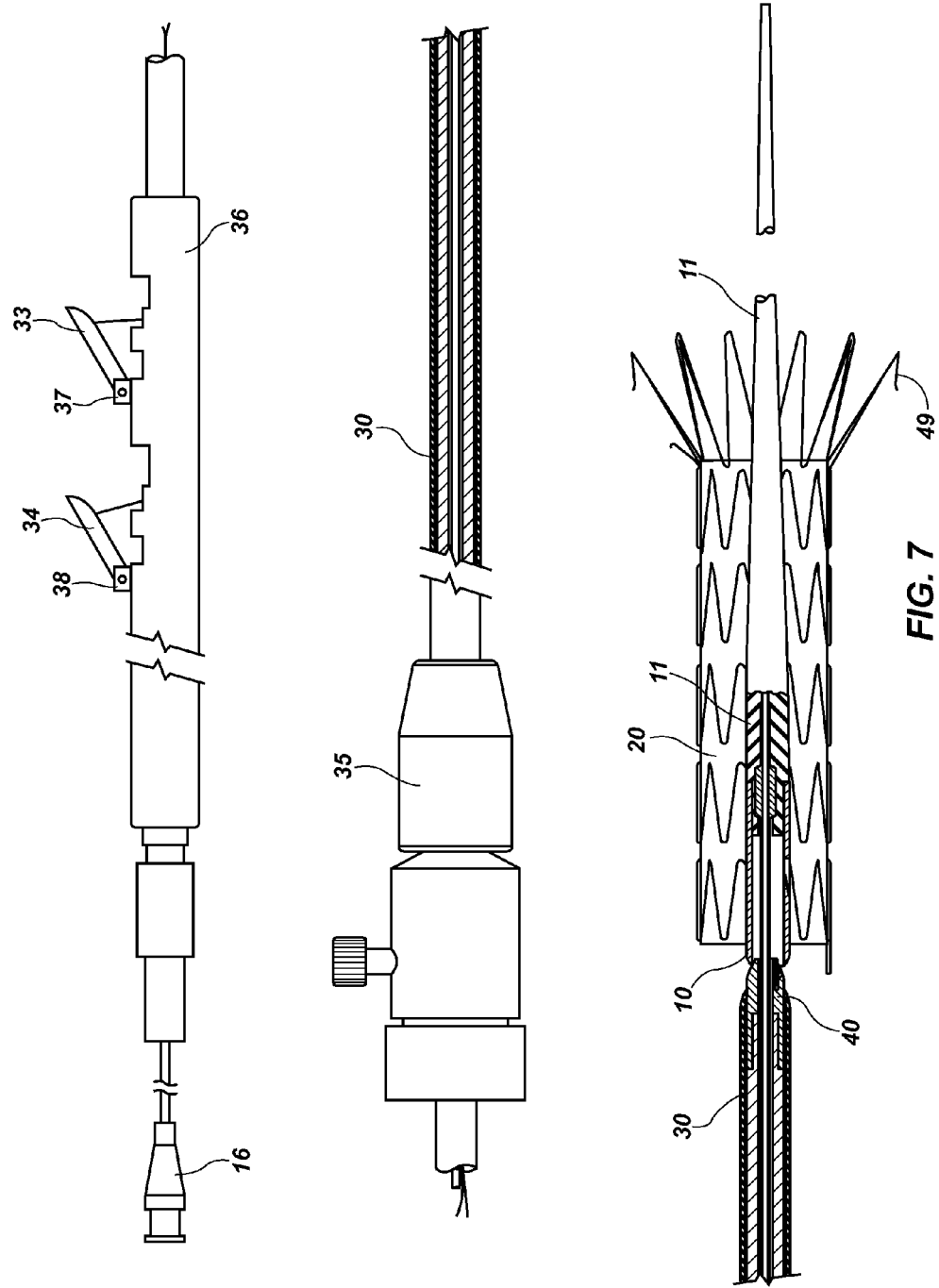
FIG. 7 shows the withdrawal of the introducer.

The first stage of removal is shown in FIG. 6, where the distal attachment device 40 is advanced to be received in the rear of the cylindrical sleeve 10, and then cylindrical sleeve 10 including the tapered flexible extension 11 and the distal attachment device 40 are removed together as shown in FIG. 7. In this drawing, the external sleeve 30 has been advanced to cover the joint between the proximal attachment device 10 and the distal attachment device 40 and is also removed with the cylindrical sleeve 10, the tapered flexible extension 11, and the distal attachment device 40. Although, these could be removed separately, and then the external sleeve 30 removed later. This may have some advantage if further surgical procedures are necessary, as a clear way is provided to advance other surgical equipment.

The size of the prostheses for use in these devices may be selected so that there is, in effect, an interference fit in the sound parts of the vessels to give good sealing onto the inner walls of the vessels. The prosthesis at its widest may range in diameter from 20 mm to 32 mm where it fits into the aorta and from 8 mm to 24 mm where it fits into the iliac arteries, for example.

Throughout this specification various indications have been given as to the scope of this invention but the invention is not limited to any one of these but may reside in two or more of these combined together. The examples are given for illustration only and not for limitation.

The invention claimed is:

1. A trigger wire release mechanism for releasing one or more retained ends of a prosthesis, the trigger wire release mechanism comprising:
   a prosthesis retaining device having proximal and distal ends and which is arranged to engage at least one end of the prosthesis;
   one or more trigger wires each having a distal end and a proximal end, the proximal end being arranged to selectively couple the prosthesis retaining device to the prosthesis;
   a control mechanism comprising an elongate body member and a lever, wherein the elongate body member has an exterior surface and an interior surface, the interior surface defining a chamber extending longitudinally with the elongate body member, and wherein the lever is connected to the elongate body member on the exterior surface with a pivot configured to be disengaged by an operator to remove the lever from the control mechanism;

wherein each of the one or more trigger wire distal ends are operably connected to the lever to selectively disengage the prosthesis retaining device from the prosthesis and wherein when the operator removes the lever, the one or more trigger wires are withdrawn from the prosthesis.

2. The trigger wire release mechanism of claim 1, wherein the elongate body member of the control mechanism further comprises at least one access passageway extending between the chamber and the lever through which each of the one or more trigger wires extends.

3. The trigger wire release mechanism according to claim 1, wherein the proximal ends of the one or more of the trigger wires are connected to the proximal end of the prosthesis retaining device.

4. The trigger wire release mechanism according to claim 1, wherein the proximal ends of the one or more of the trigger wires are connected to the distal end of the prosthesis retaining device.

5. The trigger wire release mechanism according to claim 1, wherein the one or more trigger wires include a first set of trigger wires and a second set of trigger wires, the first set of trigger wires being operably connected to the proximal end of the prosthesis retaining device and the second set of trigger wires being operably connected to the distal end of the prosthesis retaining device.

6. The trigger wire release mechanism according to claim 5, wherein the elongate body member comprises two sections, the first section comprising the lever and the first set of trigger wires, and the second section comprising a second lever pivotally connected to the elongate body member on the exterior surface.

7. The trigger wire release mechanism according to claim 6, wherein the second lever is connected to the elongate body member with a releasable pivot connection configured to be disengaged by the operator to remove the second lever.

8. The trigger wire release mechanism according to claim 5, further comprising:
a second elongate body member and a second lever, wherein the second elongate body member has an exterior surface and an interior surface, the interior surface defining a chamber extending longitudinally with the second elongate body member, wherein the chambers of the first and second elongate bodies are in fluid communication, and wherein the second lever is pivotally connected to the second elongate body member on its exterior surface, and wherein the second set of trigger wires is operably connected to the second lever.

9. The trigger wire release mechanism according to claim 8, wherein the second lever and the second elongate body member are connected with a releasable pivot connection configured to be disengaged by the operator to remove the second lever.

10. A prosthesis deployment device, comprising:
a prosthesis having proximal and distal ends, further comprising at least one self-expanding stent;
a prosthesis retaining device having proximal and distal ends and which is attachable to at least one of the proximal and distal ends of the prosthesis;
one or more trigger wires each having a distal end and a proximal end, the proximal ends of the trigger wires being arranged to selectively couple the prosthesis retaining device to at least one of the proximal or distal ends of the prosthesis;
a control mechanism comprising an elongate body member and a lever, wherein the elongate body member has an exterior surface and an interior surface, the interior surface defining a chamber extending longitudinally with the elongate body member, and wherein the lever is connected to the elongate body member on the exterior surface with a releasable pivot connection configured to be disengaged by an operator to remove the lever from the control mechanism;

wherein at least one of the one or more trigger wire distal ends is operably connected to the lever to selectively disengage the prosthesis retaining device from the prosthesis wherein when the operator removes the lever, the one or more trigger wires are withdrawn from the prosthesis.

11. The prosthesis deployment device of claim 10, wherein the elongate body member of the control mechanism further comprises at least one access passageway extending between the chamber and the lever through which at least one of the one or more trigger wires extends.

12. The prosthesis deployment device of claim 10, wherein the proximal end of at least one trigger wire is connected to the proximal end of the prosthesis retaining device.

13. The prosthesis deployment device of claim 10, wherein the proximal end of at least one trigger wire is connected to the distal end of the prosthesis retaining device.

14. The prosthesis deployment device of claim 10, wherein the one or more trigger wires include a first set of trigger wires and a second set of trigger wires, the first set of trigger wires being operably connected to the proximal end of the prosthesis retaining device and the second set of trigger wires being operably connected to the distal end of the prosthesis retaining device.

15. The prosthesis deployment device of claim 14, wherein the elongate body member comprises two sections, the first section comprising the lever and the first set of trigger wires, and the second section comprising a second lever pivotally connected to the elongate body member on the exterior surface.

16. The prosthesis deployment device of claim 15, further comprising a releasable pivot connection between the second lever and the elongate body member.

17. The prosthesis deployment device of claim 16, further comprising an external manipulation section, wherein each of the proximal and distal ends of the prosthesis retaining device are attached to the prosthesis in such a manner that the prosthesis can be held in tension therebetween and that each end of the prosthesis can individually be moved in proximal and distal directions.

18. The prosthesis deployment device of claim 14, further comprising:
a second elongate body member and a second lever, wherein the second elongate body member has an exterior surface and an interior surface, the interior surface defining a chamber extending longitudinally with the second elongate body member, wherein the chambers of the first and second elongate bodies are in fluid communication, and wherein the second lever is pivotally connected to the second elongate body member on its exterior surface, and wherein the second set of trigger wires is operably connected to the second lever.

19. The prosthesis deployment device of claim 18, further comprising a releasable pivot connection between the second lever and the second elongate body member.

20. An intraluminal deployment device, comprising:
a prosthesis having proximal and distal ends, further comprising at least one self-expanding stent;

a prosthesis retaining device having proximal and distal ends and which is attachable to at least one of the proximal and distal ends of the prosthesis;

a plurality of trigger wires each having a distal end and a proximal end, the proximal ends of the trigger wires being arranged to selectively couple the prosthesis retaining device to at least one of the proximal or distal ends of the prosthesis;

a control mechanism comprising an elongate body member and a lever, wherein the elongate body member has an exterior surface and an interior surface, the interior surface defining a chamber extending longitudinally with the elongate body member, and wherein the lever is releasably and pivotally connected to and configured with the elongate body member on the exterior surface so that an operator can remove the lever;

wherein the distal ends of the plurality of trigger wires are operably connected to the lever to selectively disengage the prosthesis retaining device from the prosthesis and wherein when the operator removes the lever, the plurality of trigger wires are withdrawn from the prosthesis.

* * * * *